(12) United States Patent
Roxhed et al.

(10) Patent No.: US 12,337,316 B2
(45) Date of Patent: Jun. 24, 2025

(54) PLASMA SEPARATING MICROFLUIDIC DEVICE

(71) Applicant: CAPITAINER AB, Solna (SE)

(72) Inventors: Niclas Roxhed, Bromma (SE); Göran Stemme, Lidingö (SE); Gabriel Lenk, Freiburg (DE); Wouter Van Der Wijngaart, Sollentuna (SE); Jonas Hansson, Stockholm (SE)

(73) Assignee: CAPITAINER AB, Solna (SE)

( * ) Notice: Subject to any disclaimer, the term of this patent is extended or adjusted under 35 U.S.C. 154(b) by 937 days.

(21) Appl. No.: 17/315,399

(22) Filed: May 10, 2021

(65) Prior Publication Data

US 2021/0260579 A1    Aug. 26, 2021

Related U.S. Application Data

(60) Division of application No. 15/847,958, filed on Dec. 20, 2017, now Pat. No. 11,000,846, which is a continuation of application No. PCT/SE2016/050591, filed on Jun. 17, 2016.

(30) Foreign Application Priority Data

Jun. 20, 2015  (SE) .................................. 1500280-1

(51) Int. Cl.
*B01L 3/00* (2006.01)
*G01N 1/40* (2006.01)
*G01N 33/49* (2006.01)

(52) U.S. Cl.
CPC ..... *B01L 3/50273* (2013.01); *B01L 3/502738* (2013.01); *B01L 3/502753* (2013.01);
(Continued)

(58) Field of Classification Search
CPC ............... G01N 1/4077; G01N 33/491; G01N 2001/4088; B01L 3/50273;
(Continued)

(56) References Cited

U.S. PATENT DOCUMENTS 5,853,670 A    12/1998    Bunce
6,084,660 A    7/2000    Shartle
(Continued)

FOREIGN PATENT DOCUMENTS

CN    104406831 A    3/2015
JP    2005-265685 A    9/2005
(Continued)

OTHER PUBLICATIONS

Lenk, G.A. et al., Delay Valving in Capillary Driven Devices Based on Dissolvable Thin Films, KTH Royal Institute of Technology, Sweden, 18th International Conference on Miniaturized Systems for Chemistry and Life Sciences, pp. 216-218 (Oct. 26-30, 2014).

*Primary Examiner* — Kathryn Elizabeth Limbaugh
(74) *Attorney, Agent, or Firm* — Porter Wright Morris & Arthur LLP

(57) ABSTRACT

A capillary driven microfluidic device with blood plasma separation means that can be used to separate, meter and transfer a blood sample. The blood separation means can be arranged as a capillary pump by the configuration of a porous membrane and the microfluidic device.

5 Claims, 3 Drawing Sheets

(52) U.S. Cl.
CPC ......... *G01N 1/4077* (2013.01); *G01N 33/491* (2013.01); *B01L 2200/025* (2013.01); *B01L 2200/0605* (2013.01); *B01L 2200/0684* (2013.01); *B01L 2300/0681* (2013.01); *B01L 2300/069* (2013.01); *B01L 2300/0864* (2013.01); *B01L 2300/0887* (2013.01); *B01L 2300/126* (2013.01); *B01L 2300/161* (2013.01); *B01L 2400/0406* (2013.01); *B01L 2400/0418* (2013.01); *B01L 2400/049* (2013.01); *B01L 2400/0677* (2013.01); *G01N 2001/4088* (2013.01)

(58) Field of Classification Search
CPC ......... B01L 3/502738; B01L 3/502753; B01L 2200/025; B01L 2200/0605; B01L 2200/0684; B01L 2300/0681; B01L 2300/069; B01L 2300/0864; B01L 2300/0887; B01L 2300/126; B01L 2300/161; B01L 2400/0406; B01L 2400/0418; B01L 2400/049; B01L 2400/0677

See application file for complete search history.

(56) References Cited

U.S. PATENT DOCUMENTS

| | | |
|---|---|---|
| 8,312,890 B1 | 11/2012 | Lau |
| 9,216,413 B2 * | 12/2015 | Blankenstein ....... G01N 33/491 |
| 2001/0001060 A1 | 5/2001 | Kellogg et al. |
| 2007/0026439 A1 | 2/2007 | Faulstich et al. |
| 2011/0011781 A1 | 1/2011 | Blankenstein et al. |
| 2012/0088227 A1 | 4/2012 | Gruebl et al. |
| 2012/0118392 A1 | 5/2012 | Blankenstein et al. |
| 2014/0224349 A1 * | 8/2014 | Ducree ............... F16K 99/0063 137/68.19 |
| 2014/0227707 A1 | 8/2014 | Yager et al. |
| 2016/0038937 A1 | 2/2016 | Ding et al. |
| 2017/0003270 A1 * | 1/2017 | Béguin ............... B01L 3/50273 |

FOREIGN PATENT DOCUMENTS

| | | |
|---|---|---|
| WO | 02/20141 A1 | 3/2002 |
| WO | 2009/106331 A2 | 9/2009 |
| WO | 2011/003689 A2 | 1/2011 |
| WO | 2011/131471 A1 | 10/2011 |
| WO | 2015/044454 A2 | 4/2015 |

* cited by examiner

PLASMA SEPARATING MICROFLUIDIC DEVICE

This application is a divisional of U.S. application Ser. No. 15/847,958, filed on 20 Dec. 2017, which is the continuation of International Application No. PCT/SE2016/050591, filed 17 Jun. 2016, which claims the benefit of Swedish Patent Application No. SE 1500280-1, filed 20 Jun. 2015, the entire contents of which are hereby incorporated by reference.

TECHNICAL FIELD

The present invention relates generally to a microfluidic device for liquids, with a capillary driven separation of blood, while generating a capillary flow of separated blood plasma.

BACKGROUND OF THE INVENTION

Microfluidic devices are used in a wide range of applications. Typically, a microfluidic device is defined to handle small fluid volumes (µL, nL, pL etc.), have a small size with at least one dimension in the micrometer range, and/or use effects of the microdomain. In such devices fluids may be moved, mixed, separated or otherwise processed. Numerous applications employ passive fluid control techniques like capillary forces.

One important area of microfluidics is in medical devices. Microfluidic devices may be used in analytical or therapeutic applications, e.g. to administer medications or to handle samples of bodily fluids.

Blood plasma based testing forms the gold standard in clinical laboratory analysis, drug development and therapeutic drug monitoring, world-wide. Plasma is usually obtained through centrifugation of venous blood samples, requiring typically milliliter samples to be taken from the patient. However, if the centrifugation step could be eliminated while still providing an analyzable and volume-defined amount of plasma, time-consuming and costly steps in clinical practice would be vastly reduced. Thus a method that only requires a microsample of blood, e.g. 50 µl obtained via fingerprick, to extract plasma is highly preferred over centrifuged plasma samples requiring milliliter volumes. Such a method would be highly relevant for billions of blood samples taken every year in laboratory analysis and drug development trials on both humans and animals.

To ensure ease-of-use and enable use in distributed settings, plasma extraction devices should preferably be autonomous, i.e. not require any external power sources, pneumatic pumps, or other additional equipment. One such autonomous system using capillary forces from surface treated polymer microchannels is described in Biomed Microdevices, vol. 8, no. 1, pp 73-79, March 2006 (S. Thorslund et al).

Different types of volume-metering capillary driven device are disclosed by WO 2015/044454 that so far only have been demonstrated with water and whole blood. There is no disclosure in WO 2015/044454 of an operable, autonomous capillary driven plasma separation process integrated with a microfluidic device, suitable in point-of-care or distributed uses.

SUMMARY OF INVENTION

The present invention is therefore directed to an autonomous microfluidic device that separates a specific volume of plasma from a blood sample of unknown volume.

In one general aspect, the invention is related to a method to separate blood plasma in which a blood separation membrane is combined with a capillary pump. Said blood separation membrane being a structure that separates blood cells and plasma. The membranes can be made from ceramics, polymers or cellulose-based materials. The capillary pump is a structure or material that provides capillary suction in order to facilitate effective plasma separation. In an embodiment of this general aspect, the membrane is applied in a geometrical arrangement that facilitates effective fluidic connection between the membrane and said capillary pump. One embodiment of this type is a geometrical structure in form of a wedge provides a high capillary force at the interesting planes between the membrane and the capillary structure. Another embodiment would include a porous material, said pores or microchannels providing high capillary force. The mentioned embodiments may include means to pinch off excess plasma from a metered plasma volume.

In aspects of the invention, other physical modalities are conceivable to enhance fluid transport across the plasma separation membrane. A first modality is having a pressure difference across the membrane by applying pressure at the inlet or having vacuum at outlet side of the membrane. Said vacuum could be stored or achieved by active means, e.g. by creating a cavity e.g. with a bellows like structure, e.g. by enabling expansion of a certain material. A second modality is to have an electric potential across the membrane. By such, an electroosmotic flow could be achieved. Another modality is providing a hygroscopic material at the outlet side of the membrane to actively suck through liquid. Such hygroscopic material could be for example PVA. The so described modalities are conceivable to combine.

In one aspect, the invention is directed to a microfluidic device with a capillary driven plasma separation means, comprising a porous membrane with an upper surface adapted to receive a blood sample and a lower surface, and a laterally extending support structure having a hydrophilic surface. The lower surface of the porous membrane and the hydrophilic surface of the support structure are configured so that the surfaces intersect in an acute angle, so the surfaces generally diverge from the intersection. When a blood sample is received in the form a droplet (at least 30 µl) on the upper surface of the membrane, plasma filtration is initiated and a lateral capillary flow of filtered fluid is formed in the proximity of the intersection of the surfaces, thereby gradually filling the space between the diverging surfaces. The plasma separation means thereby forms a capillary pump.

In this context, the lateral flow is generally perpendicular to the flow direction through the membrane and parallel to the lateral extension of the support structure of the microfluidic device. The support structure can be a hydrophilic layered material that is possible to process to a microfluidic device with several different features, as will be explained in further detail. Also in this context, the term "in the proximity" to the intersection should be understood to mean geometric conditions to initiate capillary suction from the porous membrane. This effect of initiating the lateral flow gradually filling the space between the mentioned surfaces will take place at a location where the surfaces are so close that the hydrophilic surface will intersect a fluid meniscus of a pore of the porous membrane which by estimation occurs when the gap between the surfaces is less than about 50 µm. The angle between the mentioned intersection surfaces is an acute angle, generally less than 90 degrees, preferably less than 45 degrees.

In one aspect, the so described microfluidic device, further comprises at least one capillary channel configured to receive and accommodate the lateral capillary flow arriving from the space between the diverging surfaces.

In one aspect, the microfluidic device has a capillary channel with a channel cover and a channel bottom from the laterally extending support structure and a porous membrane diagonally extends between the channel bottom and the channel cover forming a capillary wedge structure.

In one aspect, the microfluidic device has a plasma separating membrane and the support structure together forming a chamber with wedge-shaped structure. When a blood drop is applied on the membrane, the chamber is gradually filled from the intersection region of the membrane and the surface of the support structure.

In one aspect, the microfluidic devices of the invention are provided with a vent. The vent provides communication with the surrounding atmosphere and can be located in communication with the capillary channel, preferably the channel outlet.

The so described microfluidic devices can further comprise at least one dissolvable valve comprising a dissolvable membrane having a first side oriented towards the capillary channel, and capillary means connected to the second side of the dissolvable membrane such that when the membrane is dissolved by the liquid, liquid is transported through the valve to the second side of the membrane by capillary action. The capillary means comprises at least one capillary channel or a structure that allows capillary filling, such as a porous absorbent material, preferably an absorbent paper matrix. In one aspect of the invention, the capillary channel of the microfluidic device is a capillary metering channel with a defined volume having an inlet and an outlet, and a first dissolvable valve with a first dissolving time is located between the porous membrane and the capillary channel inlet and a second the dissolvable valve with a second dissolving time is located after the capillary channel outlet. For certain purposes, the microfluidic device can have a first dissolvable valve with a shorter dissolution time than the second dissolvable valve.

The microfluidic device can comprise a plurality of capillary channels arranged in parallel connected to a respective plurality of dissolvable valves, wherein capillary means of the dissolvable valves are connected to collect liquid from the valves. The microfluidic device can be formed as a laminate comprising a first layer of material forming the capillary channel, a second layer of material comprising dissolvable material, to form the at least one dissolvable membrane, and a third layer of material comprising the capillary means.

The so described microfluidic devices can further comprise at least one dissolvable valve comprising a dissolvable membrane having a first side oriented towards the capillary channel, and capillary means connected to the second side of the dissolvable membrane such that when the membrane is dissolved by the liquid, liquid is transported through the valve to the second side of the membrane by capillary action. The capillary means comprises at least one capillary channel or a structure that allows capillary filling, such as a porous absorbent material, preferably an absorbent paper matrix.

In one aspect of the invention, the capillary channel of the microfluidic device is a capillary metering channel with a defined volume having an inlet and an outlet, and a first dissolvable valve with a first dissolving time is located between the porous membrane and the capillary channel inlet and a second the dissolvable valve with a second dissolving time is located after the capillary channel outlet. For certain purposes, the microfluidic device can have a first dissolvable valve with a shorter dissolution time than the second dissolvable valve. The microfluidic device can comprise a plurality of capillary channels arranged in parallel connected to a respective plurality of dissolvable valves, wherein capillary means of the dissolvable valves are connected to collect liquid from the valves.

The microfluidic device can be formed as a laminate comprising a first layer of material forming the capillary channel, a second layer of material comprising dissolvable material, to form the at least one dissolvable membrane, and a third layer of material comprising the capillary means.

In one aspect, the microfluidic device according of the invention is provided so that the upper surface of the porous membrane is aligned with an absorbent pad or adsorbent structure, adapted to receive the blood sample. The absorbent pad can be essentially circular or donut-shaped in order to guide or assist the user to more precisely put a blood droplet on the device.

Thus, the invention relates to a microfluidic device comprising a plasma separation arrangement forming a capillary pump, a capillary channel in fluid connection therewith, the channel having a defined volume, at least one dissolvable valve comprising a dissolvable membrane. The dissolvable membrane comprises material dissolvable by the liquid and has a first side oriented towards, i.e. facing, the capillary channel. A capillary means is connected to the second side of the dissolvable membrane such that when the membrane is dissolved by the liquid, liquid is transported through the valve to the second side of the membrane by capillary action.

The so described microfluidic devices can further comprise at least one dissolvable valve comprising a dissolvable membrane having a first side oriented towards the capillary channel, and capillary means connected to the second side of the dissolvable membrane such that when the membrane is dissolved by the liquid, liquid is transported through the valve to the second side of the membrane by capillary action. The capillary means comprises at least one capillary channel or a structure that allows capillary filling, such as a porous absorbent material, preferably an absorbent paper matrix. In one aspect of the invention, the capillary channel of the microfluidic device is a capillary metering channel with a defined volume having an inlet and an outlet, and a first dissolvable valve with a first dissolving time is located between the porous membrane and the capillary channel inlet and a second the dissolvable valve with a second dissolving time is located after the capillary channel outlet. For certain purposes, the microfluidic device can have a first dissolvable valve with a shorter dissolution time than the second dissolvable valve.

The microfluidic device can comprise a plurality of capillary channels arranged in parallel connected to a respective plurality of dissolvable valves, wherein capillary means of the dissolvable valves are connected to collect liquid from the valves. The microfluidic device can be formed as a laminate comprising a first layer of material forming the capillary channel, a second layer of material comprising dissolvable material, to form the at least one dissolvable membrane, and a third layer of material comprising the capillary means.

The dissolvable membrane with the capillary means thus form a dissolvable valve. The capillary channel and the dissolvable valve cooperate to define a volume of liquid transported through the capillary channel. Thus the volume of liquid transported through the capillary channel is a portion of the liquid supplied to the inlet port.

The capillary channel is suitable for metering a volume of liquid drawn therein by capillary action from the inlet port. The dissolvable membrane has a lateral extension which is larger than a thickness dimension of the membrane in order to facilitate dissolution and fabrication of the device. It thus has a first and a second side. The material of the membrane is dissolvable by liquid in a time frame that is reasonable for the device to function, i.e. less than 1 hour, less than 10 minutes or less than 1 minute, depending on application. By dissolving the membrane, it is understood that the membrane is dissolved sufficiently to uncover the capillary means connected to the second side of the membrane. With capillary it is meant a structure which is configured to drive liquid flow by capillary action.

The microfluidic device may comprise an air vent before each dissolvable membrane to allow for capillary filling of liquid up to the membrane.

Thus the dissolvable membrane may be used to cancel fluid communication with the capillary channel, thus providing a "pinch-off" effect of liquid in the capillary channel to define a volume already entered into the capillary channel.

The capillary channel may have an inlet portion, connected to the capillary pump, and an outlet portion, and wherein the at least one dissolvable valve is in capillary connection to the outlet portion of the capillary channel, and arranged for transporting liquid from the capillary channel when the membrane is dissolved.

Thus the capillary channel may be filled to define a volume of liquid in the device, followed by release of the volume of liquid through the dissolvable membrane.

The capillary means may comprise at least one capillary channel or a structure that allows capillary filling, such as a porous absorbent material, preferably an absorbent paper matrix.

Thus liquid may be effectively transported over the dissolvable membrane once dissolved. Liquid may e.g. be collected in the porous material for further analysis.

The device may comprises a plurality of capillary channels arranged in parallel connected to a respective plurality of dissolvable valves, wherein capillary means of the dissolvable valves are connected to collect liquid from the valves.

Thus the liquid volumes defined before the valves may be released sequentially or in parallel e.g. to perform a predetermined sequence of reactions in the device.

The microfluidic device may comprise a plurality of dissolvable valves, distributed along a capillary flow path of liquid in the microfluidic device, comprising the capillary channel.

Thus sequential processing of liquid in the device may be performed.

The capillary channel may comprise a branched capillary channel structure comprising a plurality of side arms capillary connected to the plurality of dissolvable valves.

Thus the liquid volume may be divided into a plurality of sub volumes for further processing in the device.

The dissolution times of the plurality of dissolvable membranes of the valves may be individually tailored to provide a predetermined timing of events in the microfluidic device. The plurality of dissolvable membranes of the valves may be individually tailored with different membrane thicknesses to provide the different dissolution times.

Thus fluidic operations may be performed in a timed and sequential fashion to allow for advanced fluidic multistep procedures in the device.

The first side of the at least one dissolvable membrane of the valve may be connected to a capillary dead end channel, configured such that liquid dissolving the membrane is transported into the capillary dead end channel by capillary forces.

Thus liquid loaded with dissolved material of the membrane may be led into the capillary dead end channel to allow for liquid having less amount of dissolved material to propagate through the membrane once dissolved. Thus, e.g. the viscosity of the liquid may be maintained.

If the device comprises a plurality of the dissolvable membranes, more than one dissolvable membrane may be connected to a respective capillary dead end channel.

Thus, at every dissolvable membrane, e.g. along a flow path of liquid in the device, the liquid loaded with dissolved material of the membrane may be led into a respective capillary dead end channel.

The material of the dissolvable membrane may be dissolvable by bodily fluid, when the liquid is a bodily fluid, such as blood.

The material of the dissolvable membrane may comprise polyvinyl alcohol (PVA), dissolvable polysaccharides, gelatin and the like.

The material of the dissolvable membrane may comprise at least one substance to be released into the liquid, such as one or more regents and/or one or more particles.

Thus, once dissolved, the substance may be released into the liquid passing the membrane.

At least one region of dissolvable material comprising at least one substance to be released into the liquid, such one or more regents and/or one or more particles, may be distributed along a flow path of liquid in the microfluidic device.

Thus the device may be provided with substance-loaded dissolvable material at various regions along a flow path of liquid in the device, to be released by liquid dissolving the dissolvable material. The material may e.g. be provided as films along a fluid channel or in a fluid chamber.

The membrane of the valve or dissolvable region may comprise a multilayer structure comprising different substances to be released into the liquid.

The device may comprise at least one at least one storage of a substance, such as one or more regents and/or one or more particles, and at least one dissolvable membrane provided to seal the at least one storage, wherein the substance is to be released into the liquid by dissolving the membrane.

Thus the release of liquid substances into the liquid may be triggered by liquid dissolving a membrane sealing a storage chamber for the substance.

The microfluidic device may comprise a laminate of layers of material defining a flow path for the liquid and comprising at least one layer of dissolvable material forming the at least one dissolvable membrane.

Thus one or more membranes may be formed in a simple manner in the microfluidic device.

The microfluidic device may comprise a plurality of dissolvable membranes formed by one and the same layer of dissolvable material in the microfluidic device.

The capillary flow path in the microfluidic device may comprise capillary channels on both sides of the dissolvable membrane layer, wherein a plurality of dissolvable valves are formed at flow path crossings across the dissolvable membrane layer.

Thus a plurality of dissolvable membranes and capillary channels may be formed in a simple manner in the device.

The invention further relates to a microfluidic device including the mentioned plasma separation means, comprising a metering capillary channel having a first and a second end, a first dissolvable membrane at the first end, an outlet port connected to the second end of the metering capillary channel, a second dissolvable membrane connected to the outlet port, capillary means for removing liquid when the respective dissolvable membrane is dissolved by the liquid, wherein the dissolvable membranes and the metering capillary channel are configured such that the first membrane is dissolved before the second membrane by a liquid supplied to the inlet.

Thereby liquid provided at the inlet of the capillary channel starts dissolving the first dissolvable membrane while a portion of liquid provided at the inlet is drawn into the capillary channel to reach the second dissolvable membrane. The device is configured such that the first dissolvable membrane is dissolved by liquid at the inlet before the second dissolvable membrane is dissolved by liquid drawn in through the capillary channel. Thus excess liquid is transported from the inlet through the first dissolved membrane by the capillary means for removing liquid from the inlet. The volume of liquid in the capillary channel is thus "pinched off", i.e. forming a free liquid surface facing the inlet. Thereafter the second dissolvable membrane is dissolved, whereby the defined volume of liquid in the metering capillary is drawn from the capillary channel by the capillary means for removing liquid from the outlet port. A defined volume of liquid is thus separated from the undefined volume of liquid provided at the inlet.

The microfluidic device can generally comprise at least one metering capillary channel (having a first and a second end) and a first side of a first dissolvable membrane (having a first and a second side) and where the second end of the metering capillary channel is connected to a vent port and a first side of a second dissolvable membrane. The second sides of the membranes are connected to channels, structures or materials with capillary functionality. The dimensions of the metering channel and the material, thicknesses and areas of the dissolvable membranes are chosen so that the first membrane is dissolved before the second membrane when a liquid is presented to the inlet port.

The microfluidic device can comprise a microfluidic channel, where said channel introduces a time delay for the liquid to propagate, dissolvable regions where said dissolvable regions introduce certain time delays, and where the device may have a singularity or a plurality of said dissolvable regions, said regions being realized by for example a thin film of a resorbing polymer material (e.g. PVA). These different regions may thus provide means for having delayed events occurring in the device enabling handling of for example excess liquid.

The dissolvable region may be in contact with a structure that allows capillary filling once said region has been dissolved. The structure that allows capillary filling may be for example paper, cotton matrix, a hydrophilic micro channel or another porous medium allowing further liquid propagation by capillary action.

The microfluidic device may be formed as a laminate comprising a first layer of material forming the capillary channel, a second layer of material comprising dissolvable material, to form the at least one dissolvable membrane, and a third layer of material comprising the capillary means. Thus the device may be fabricated in a simple manner. A method of fabricating a microfluidic device as disclosed herein comprising the steps of providing a first layer of material forming the capillary channel, providing a second layer of material comprising dissolvable material, to form the at least one dissolvable membrane, providing a third layer of material comprising the capillary means, and laminating the first, second and third layers of material, and any further layers such as cover layers, spacing layers, and/or further layers of material forming fluidic functions in the device, thereby forming a laminate comprising the microfluidic device. Thus the microfluidic device may be fabricated in a simple and cost-efficient manner, suitable for mass fabrication. The third layer of material may comprise at least one capillary channel or a structure that allows capillary filling, such as a porous absorbent material, preferably a layer of absorbent paper. The lamination may be performed with a bonding region between two layers in the laminate, preferably comprising a heat or pressure sensitive adhesive, a reactive adhesive, wax of formed by means of surface activation or thermocompression. The lamination may be performed in several subsequent steps of aligning and laminating the layers of material of the laminate.

The present invention also relates to a method of preparing a sample from whole blood comprising the steps of in previously disclosed microfluidic device, arranging a porous blood plasma separating membrane in an acute angle with a hydrophilic surface of a support structure; applying at least 30 µl whole blood to an upper surface of the membrane and admitting separation of plasma through the membrane; admitting a wedge-shaped space between the membrane and the support structure gradually be filled with separated plasma; and filling a capillary channel in fluid communication with said space with separated plasma.

The method can further comprise cancelling the fluid communication between the wedge-shaped space and capillary channel by dissolving a dissolvable valve at the capillary channel inlet.

The method can further comprise dissolving a second dissolvable valve at outlet of the capillary channel.

The method can further comprise transporting a metered volume of separated to plasma to a capillary means to form a volume defined plasma spot.

DETAILED DESCRIPTION OF EMBODIMENTS

In the following, a detailed description of embodiments of the invention is disclosed.

Device Fabrication

The microfluidic layer consists of hydrophilic XEROX® copier transparencies (003R96002 Type C, Xerox Co. Ltd., USA) and a capillary spacer tape (IVD 090448PV1.001/09, Tesa GmbH, Germany). The different layers were structured separately with a cutting plotter (CE5000, Graphtec America Inc., USA) and laminated together with a laminator (H600, GBC Inc., USA). A liquid PVA solution was prepared from PVA granule (MOWIOL® 4-88 Mw ~31,000, Sigma Aldrich Inc., USA) by dissolving it in DI water and was then spin-coated onto silicon wafers and dried to form thin dissolvable films. The film thickness controlling the dissolving time was fitted to the filtration times required to fill the plasma volume in the metering channel. The dissolvable films were laminated to the microfluidic layer at the openings in the bottom of the channel forming the two dissolvable valves. The microfluidic layer was then attached to the chip backing holding the paper patches (Whatman 903, GE Healthcare, USA) which were used as capillary substrate to absorb the excess plasma and the metered plasma. A 9×9 mm2 large square of the filtration membrane (SG membrane, from iPOC, Canada) was attached to the inlet of the chip so that the filter forms a capillary wedge structure together with the channel bottom. For attaching the filtration membrane to the chip, double sided adhesive tape (IVD 090448PV1.001/09, Tesa GmbH, Germany) was used.

Filter to Channel Interface Testing

To study the liquid connection formation between the filter and the capillary channel, the wedge structure was observed by filming the device from the side and through the transparent bottom.

Plasma Extraction Efficiency Testing

Figure 1:
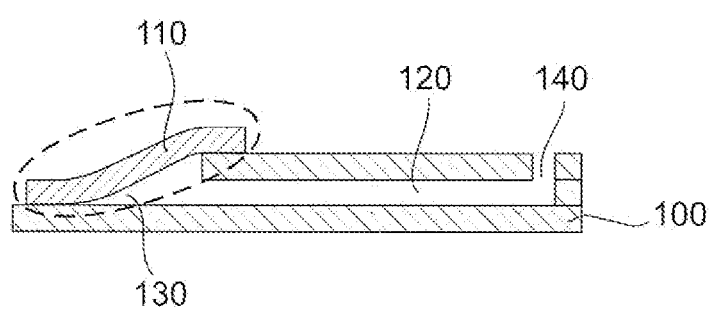
FIG. 1 shows a general embodiment employing a plasma separating membrane arranged according to the invention with a capillary channel. The test structures are assembled for an extraction efficiency experiment.
Figure 2:
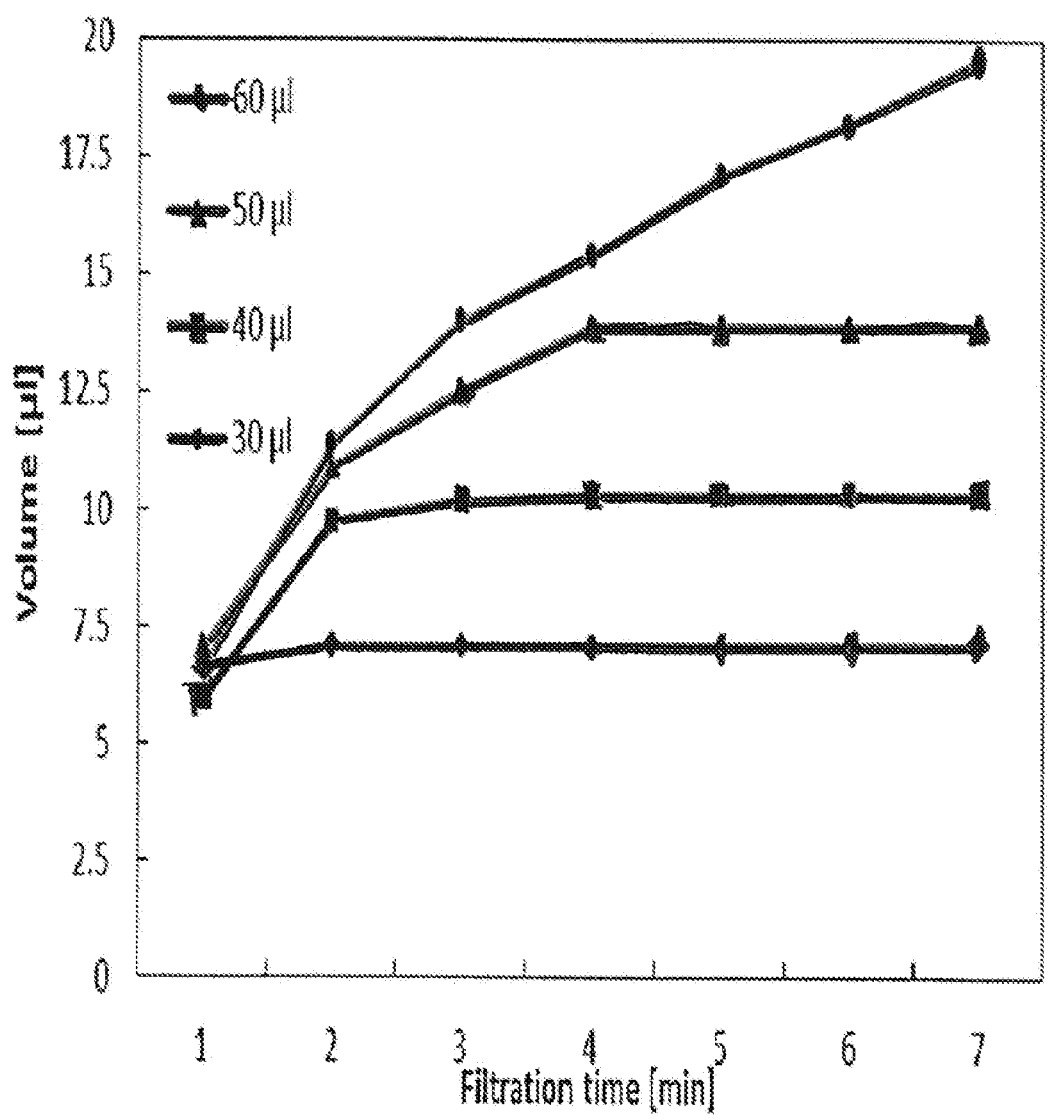
FIG. 2 shows plasma extraction kinetics of an iPOC filter together with capillary channels.
Figure 3A:
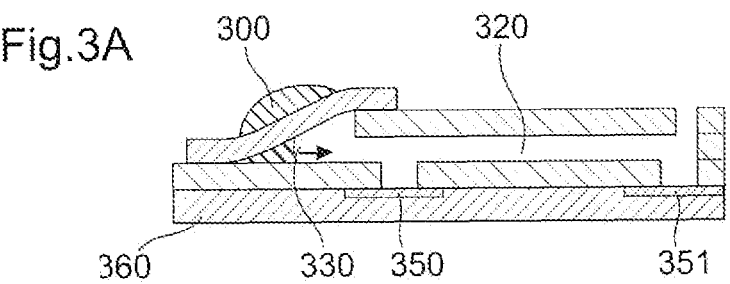
FIGS. 3A-3F show schematic cross sections of the plasma extraction metering chip.
Figure 3B:
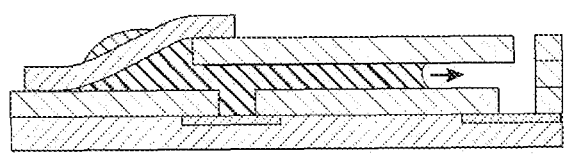
Figure 3C:
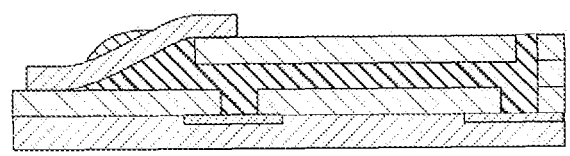
Figure 3D:
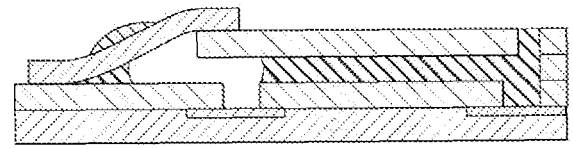
Figure 3E:
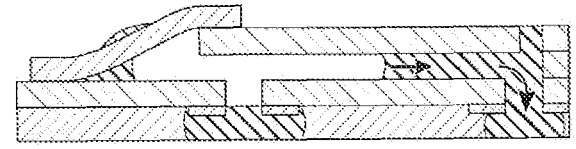
Figure 3F:
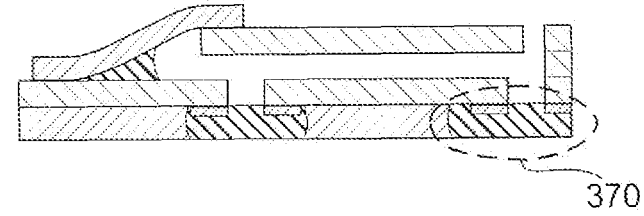

For measuring the extraction efficiency of the filtration membrane, capillary channels without metering function were used (no dissolving valves were used) as seen in the device in FIG. 1. Different volumes (30-60 µl) of venous human blood, drawn in EDTA-treated tubes were applied to the top of the filtration membrane. Plasma volumes and filtration times were extracted from video recordings.

For the proof-of-concept, 50 µl of fresh capillary blood from a fingerprick was applied to a chip as shown in FIG. 1 and FIG. 3. A video recording from the top was used to verify correct timing of different events and correct chip function.

The device is shown in FIG. 1 and its working principle is further illustrated in FIG. 1. For plasma separation and volume metering, starting from a non-metered droplet of blood, several consecutive events are pre-programmed in the device design. FIG. 1 shows a general microfluidic device with a capillary driven plasma separation means according to the invention. The Microfluidic device has a support structure 100, a porous membrane (filter) 110, a capillary channel 120 and a vent 140. The porous membrane is arranged at an acute angle with the upper hydrophilic surface of the support structure. The support structure 100 laterally extends from the intersection with the filter 110 and generally provides a channel cover and a channel bottom for the capillary channel 120.

Referring to FIG. 1, when adding a droplet of blood to the application side of the filter 110, the plasma in the blood is drawn through the filter by capillary forces, leaving the blood cells mechanically stuck in the filter. The capillary fluidic connection between a filter and a capillary channel is challenging. For the purpose of the present invention, the filter is attached diagonally in the microfluidic device at the inlet of the capillary channel, forming a capillary wedge-structure 130 between channel bottom and channel cover. The contact area between the filter and the channel bottom forms a capillary bridge that allows the plasma to leak out of the filter pores and gradually fill the wedge structure 130 from the contact point to the channel inlet.

The plasma extraction in the test device without dissolvable valves, seen in FIG. 1, works for the whole range of tested volumes, 30-60 µl (see FIG. 4). For 60 µl of whole blood, 19.5 µl of plasma could be extracted. For 30 µl of applied blood, 7.1 µl of plasma was extracted. Increasing plasma extraction efficiency for higher applied blood volumes can be explained by the dead volume in and under the filtration membrane. To ensure correct functioning of the plasma-extraction and metering chip, its microchannel was designed to have a metering volume of 4 µl.

Applying at least 30 µl of whole blood to the plasma separation membrane resulted in plasma filling of the microchannel. Applying less than 30 µl is insufficient for channel filling, most likely because of the dead volume under the membrane and the dead volume of the filtration membrane itself.

The wedge structure formed between the plasma filter and the channel bottom provides a good capillary contact between the filter and the channel. It is clearly observable how separated plasma propagates from the narrowest part of the wedge structure where the capillary force is the highest and gradually fills up to the channel inlet.

Volume Metered Plasma Extraction Testing

As a next step, a plasma extraction and metering microfluidic chip is formed, see FIG. 3 with similar features as disclosed WO 2015/044454. In FIGS. 3A-C, a droplet of blood 300 is applied to the filtration membrane and it initiates plasma extraction along the capillary wedge 330 into the metering channel 320. The next, and most crucial step for volume metering, is to successfully separate metered plasma from excessive plasma. Two dissolvable valves 350, 351 at the bottom of the channel, separate the capillary channel from an absorbent paper 360, see FIG. 3. Wetting of each of the valves initiates a dissolving process, which opens the valve, thereby connecting the channel to the paper. When the metering channel 320 starts to fill with plasma the first valve 350 located closest to the channel inlet comes in contact with plasma first. Delayed by the time required to fill the volume of the channel with plasma, the second valve 351 is wetted and starts to dissolve. The device is designed such that the valve dissolving times, defined by the valve thicknesses, as described in WO 2015/044454, are larger than the capillary channel filling time, thus ensuring that the entire capillary channel is filled before the first valve is opened. Opening of the first valve at the inlet of the channel drains all upstream plasma, i.e. between the first valve and the wedge structure, into an absorbent paper substrate, while the metered plasma remains trapped in the microchannel, see FIG. 3C. Opening of the second valve drains the volume-metered plasma in the channel at the outlet of the second valve forming a volume defined plasma spot 370, see FIGS. 3E and 3F. Additionally, the first valve prevents any refilling of the metering channel by immediately draining any newly filtered plasma.

It can be concluded that the present invention, provides an easy-to-use sampling device, which is able to (a) separate plasma from unprocessed human whole blood and (b) meter a defined volume of the plasma for further processing or downstream analysis. The completely autonomous working principle of the chip enables new possibilities by reducing required sample volumes, allowing point-of-care plasma extraction and offering an alternative to venous blood processing by centrifugation. This is highly relevant for clinical laboratory analysis but especially in the field of therapeutic drug monitoring and drug development where the demonstrated principle can help to eases the collection of high quality data while being beneficial for patients.

The invention claimed is:

1. A method of preparing and transporting a sample from whole blood comprising the steps of:
   (i) arranging in a microfluidic device, a substantially flat porous membrane so that a lower surface of the porous membrane forms an intersection in an acute angle with a hydrophilic surface of a support structure, wherein said porous membrane extends diagonally between a channel bottom and a channel cover of a capillary channel configured to receive and accommodate a lateral capillary flow, wherein a portion of the lower surface of the porous membrane contacts a top of the channel cover;
   (ii) applying at least 30 µl whole blood to an upper surface of the membrane and admitting separation of plasma through the membrane;
   (iii) admitting a wedge-shaped space between the membrane and the support structure to be gradually filled with separated plasma; and
   (iv) filling the capillary channel in fluid communication with said wedge-shaped space and metering a defined volume of separated plasma.

2. The method of claim 1, further comprising cancelling fluid communication between the wedge-shaped space and the capillary channel by pinching off excess plasma from the defined volume in the capillary channel.

3. The method of claim 1, further comprising cancelling the fluid communication between the wedge-shaped space and capillary channel by dissolving a dissolvable valve at the capillary channel inlet.

4. The method of claim 1, further comprising dissolving a dissolvable valve at the outlet of the capillary channel.

5. The method of claim 1, comprising transporting a metered volume of separated plasma to a capillary means to form a volume defined plasma spot.

* * * * *